(12) United States Patent
Duval et al.

(10) Patent No.: US 6,342,592 B1
(45) Date of Patent: *Jan. 29, 2002

(54) CHIRAL COMPOUNDS, THEIR SYNTHESIS AND USE AS A SUPPORT

(75) Inventors: Raphaël Duval, Notre Dame de Gravenchon; Hubert Leveque, Lillebonne, both of (FR)

(73) Assignee: Institut Francais du Petrole and Chiralsep (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/039,266

(22) Filed: Mar. 16, 1998

(30) Foreign Application Priority Data

Mar. 14, 1997 (FR) .............................. 97 03076

(51) Int. Cl.⁷ .............................................. C07H 15/00

(52) U.S. Cl. .......................... 536/22.1; 514/42; 536/53; 562/471; 562/473

(58) Field of Search ................................. 562/471, 473; 514/42; 536/22.1, 53

(56) References Cited

U.S. PATENT DOCUMENTS

| 4,518,758 A | * 5/1985 | Cavezzan et al. ............. 528/12 |
| 4,710,491 A | * 12/1987 | Lockhoff et al. ............. 514/42 |
| 4,737,488 A | * 4/1988 | Lockhoff et al. ............. 514/42 |

FOREIGN PATENT DOCUMENTS

| FR | 2 394 523 | 1/1979 |
| JP | 5-271307 | 10/1993 |

OTHER PUBLICATIONS

Ellis et al, J. Med. Chem., 10(1), pp. 130–131, 1967.*

Kumar et al, J. Am. Chem. Soc., 114(17), pp. 6630–6639, 1992.*

Kelly et al, Helv. Chim. Acta, 71(2), pp. 461–466, 1988.*

Patent Abstracts of Japan, Abstract No. 365255 (JP 05271307), vol. 18, No. 46 (C–1157), Jan. 25, 1994.

Yi et al., "Large–rim–tethered permethyl–substituted β–cyclodextrin polysiloxanes for use as chiral stationary phases in open tubular column chromatography", *J. of Chromatography*, vol. 673:219,230, 1994.

* cited by examiner

*Primary Examiner*—Shailendra Kumar
(74) *Attorney, Agent, or Firm*—Millen, White, Zelano & Branigan, P.C.

(57) ABSTRACT

The invention relates to a method which comprises synthesising bifunctional compounds then chiral compounds from the bifunctional compounds, also to synthesising supports comprising these chiral compounds, and the use of these supports for preparing or separating enantiomers, or for asymmetric synthesis. The invention also relates to bifunctional compounds, their use as a source of functionalised polymers, and to the chiral compounds, also to the use of these chiral compounds in a chiral support in the form of a three-dimensional network or for separating or preparing enantiomers, principally for analytical or preparative chromatography, and in a support for the production of chiral molecules by asymmetric synthesis.

24 Claims, 5 Drawing Sheets

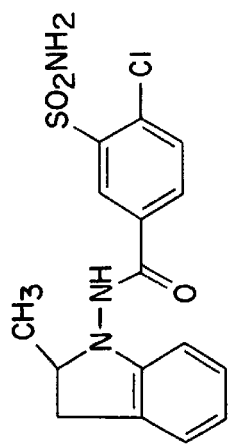
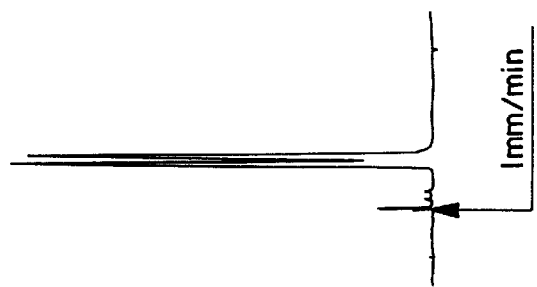
FIG. ID
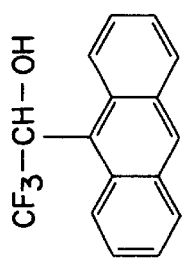
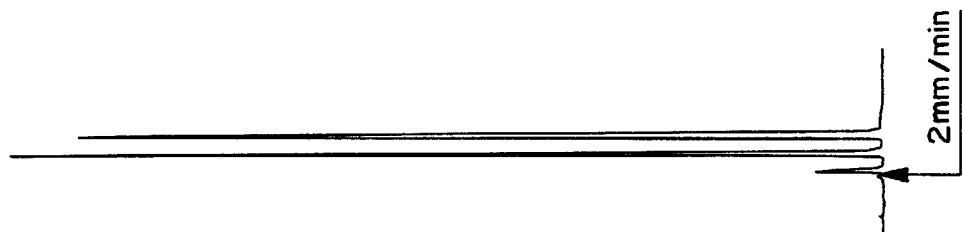
FIG. IC

CHIRAL COMPOUNDS, THEIR SYNTHESIS AND USE AS A SUPPORT

FIELD OF THE INVENTION

The invention relates to a method which comprises synthesising bifunctional compounds then chiral compounds from the bifunctional compounds, also to synthesising supports comprising these chiral compounds, normally in the form of a cross-linked three-dimensional chiral network and generally with a modifiable degree of cross-linking depending on the desired degree of swelling, and the use of these supports for preparing and separating enantiomers, or for asymmetric synthesis. The invention also relates to bifunctional compounds, their use as a source of functionalised polymers, and to the chiral compounds, also to the use of these chiral compounds in a chiral support for separating and preparing enantiomers, principally for analytical or preparative chromatography, and for asymmetric synthesis.

BACKGROUND OF THE INVENTION

Enantiomer separation is a field which has been expanding for about twenty years both on the preparative and on the analytical levels. This is particularly true in the pharmaceutical field, where the law requires the separate study of optical isomers of any chiral component of a medication composition. Substituted polysaccharides have been the subject of a number of studies, and celluloses physically deposited on a silica gel support are commercially available. Such compounds have the disadvantage, however, of usually being soluble in polar organic solvents, which drastically limits their applications.

Recent solutions to the problem of solubility have been found by forming covalent bonds between the substituted polysaccharide and the support. Kimata et al. have published their results ("Analytical methods and instrumentation", vol. 1, 23–29 (1993)) on a stationary chiral phase based on -tris-2,3,6(4-vinylbenzoate) cellulose deposited on silica gel, then polymerised on the support.

Chromatographic data obtained with two racemic test mixtures were as follows:

|  | Deposited support | | Deposited and polymerised support | |
|---|---|---|---|---|
|  | Stilbene oxide | 1-(1-naphthyl) ethanol) | Stilbene oxide | 1-(1-naphthyl ethanol) |
| k'1 | 1.08 | 2.15 | 1.04 | 1.47 |
| k'2 | 1.66 | 2.84 | 1.44 | 1.80 |
| α | 1.54 | 1.32 | 1.39 | 1.22 |
| R$_S$ | 3.63 | 2.34 | 3.82 | 1.44 | where:

k'1 and k'2 are partition ratios, i.e., if i=1 or 2, $$k'_i = \frac{t_{Ri} - t_0}{t_o}$$

where $t_{Ri}$ is the retention time of compound i; and $t_0$ is the non-retained solute transit time;

α is the relative retention ratio:

$$\alpha = \frac{t_{R2} - t_0}{t_{R1} - t_0} = \frac{k'2}{k'1}$$

R$_S$ is the peak resolution:

$$R_S = \frac{1}{4}\left(\frac{\alpha - 1}{\alpha}\right)\left(\frac{k'2}{1+k'2}\right)(N)^{\frac{1}{2}}$$

where N is the plate number $$N = a\left(\frac{t_R}{\omega}\right)^2$$

where ω is the peak width at a given ordinate, related to the square of the standard deviation or variance $\sigma^2$ by the relationship $\omega^2 = a\sigma^2$, giving $$N = 16\left(\frac{t_R}{\omega}\right)^2 = 5.54\left(\frac{t_R}{\sigma}\right)^2$$

A systematic reduction in the relative retention ratios obtained can be seen between the deposited support and the deposited and polymerised support: 10% less on the trans-stilbene oxide (α varies between 1.54 and 1.39) and 25% less for the 1-(1-naphthyl)ethanol.

This phenomenon can be explained by partial solubility of the polymerised support due to incomplete polymerisation because of weak reactivity of the vinyl benzoate group under the reaction conditions used.

Kimata et al. did not describe any examples of separation in a pure polar solvent.

Okamoto et al. (in European patent EP-B-0 155 637) described polymers which are chemically bonded to a silica gel. In particular, they described grafting tris-2,3,6-phenylcarbamate cellulose onto silica gel via a tritylated intermediate, then forming a covalent bond between the silica gel and the partially derived polysaccharide carbamate, by the action of a diisocyanate.

The results of elemental analyses carried out during the different stages of synthesis were as follows (EP-B-0 155 637, page 8 to page 9, line 33).

|  | C% | H% | N% |
|---|---|---|---|
| 1. Trityl cellulose deposited on silica | 15.40 | 1.23 | 0.09 |
| 2. Detritylated cellulose deposited on silica | 3.61 | 0.60 | — |
| 3. Cellulose bonded to silica by toluene-2,4-diisocyanate | — | — | — |
| 4. Cellulose phenyl carbamate bonded to silica and washed with THF/chloroform | 3.23 | 0.27 | 0.45 |

The drop in the degree of grafting between the cellulose deposited on silica (2) and cellulose phenylcarbamate bonded to silica (4) is important knowing that the degree of (4) calculated after (2) is of the order of 14% of carbon. The loss of hydrocarbon moieties can thus be estimated to be 80% from formation of the covalent bond between the cellulose and the silica by the diisocyanate arm, followed by derivative formation by reacting the OH groups with phenyl isocyanate and final washing with chloroform.

No example of separation in polar solvents was given for the support obtained.

Okamoto et al (Japanese patent JP 06-206-893) have described an oligosaccharide chemically bonded to silica gel by means of an imine function reduced to an amine. Amylose is then chemicoenzymatically regenerated from this oligosaccharide. The available hydroxyl functions are then reacted with carbamate functions to form derivatives. No example of separation in a polar solvent was given.

It is important to use a large column excess for preparative applications. The possibility of using 100% of chiral material in the form of pure polymer beads of substituted polysaccharides instead of physically depositing them on a support has proved effective in increasing mass yields in preparative chiral chromatographic processes. Thus patents EP-B-0 348 352, EP-B-0 316 270 and International patent application WO 96/27639 relate to the production of cellulose beads for separating optical isomers.

However, pure polymer beads are soluble in polar solvents such as halogenated solvents—tetrahydrofuran, dioxane, etc. It is thus impossible to use these solvents either pure or in mixtures with high proportions of these solvents, to carry out isomer separation.

In order to overcome this disadvantage, Francotte et al. recommended irradiation polymerisation of polysaccharide derivatives. (WO 96/27615).

However, the degree of polymerisation appears to be difficult to control in such a process. No example of separation in a pure polar solvent is given.

Minguillon et al. described the synthesis of cellulose carbamates with partial derivatives formed by reaction with an undecenoyl chloride. However, the structure of the support was not explained (J. of Chromatog. A 728 (1996), 407–414 and 415–422).

Lange (U.S. Pat. No. 5,274,167) described the polymerisation of optically active methacrylic acid derivatives, but the structure of the support was not explained. No example of separation in a pure polar solvent was given.

The present invention concerns the preparation of novel chiral compounds and their use in preparing or separating enantiomers, in particular on a support or in polymer beads.

SUMMARY OF THE INVENTION

The chiral supports are obtained in the form of pure polymer beads of the chiral compound which is normally polymerised and cross-linked, preferably into a three-dimensional glycosidic network or obtained in the form of a chiral compound attached to a support via a covalent bond, then polymerised and cross-linked, preferably into a three-dimensional glycosidic network.

The chiral supports of the invention have remarkable stability in polar solvents such as TIF (tetrahydrofuran), chloroform, methylene chloride, acetonitrile, toluene, acetone or ethyl acetate.

For the first time, separation of a racemic molecule on a support based on a polysaccharide has been carried out in pure chloroform (see Examples IA, IB, IC and ID).

This exceptional stability towards polar solvents of the novel chiral supports is associated with the extremely fast mass transfer kinetics between the solutes and the three-dimensional glycosidic network. Again for the first time, separations have been carried out in the normal or inverse mode using an elution gradient on stationary chiral phases (see Examples IIA and IIB).

Further, we have noticed that the degree of cross-linking of the chiral supports has an influence on the swelling capacity of the supports. Since the swelling capacity is variable, there are difficulties in using it for analytical or preparative purposes in chromatographic processes: variable support volume, and the creation of large pressure drops during swelling can result in columns which are of insufficient size exploding or percolation becoming impossible for those which resist high pressures; also, during shrinking, dead volumes are seen to form which are incompatible with their current use.

The possibility of modifying the number and nature of the bifunctional compounds ensuring polymerisation and cross-linking per chiral unit has the advantage of enabling the degree of cross-linking and thus the final performance of the chiral support to be modified and in particular the swelling capacity in polar solvents can be controlled.

Further, we have noticed that the use of polar solvents mixed with other alkane/alcohol type solvents can in some cases reverse the elution order of enantiomers of compounds of biological importance (see Example III). When analysing the enantiomeric purity of chiral molecules, the gain in sensitivity is thus significant. The compound which is eluted first is always that with a higher number of theoretical plates than the second.

For the same reasons, the first enantiomer eluted in a preparative chiral chromatographic process is always the most pure and the most concentrated. There is thus a major interest in analytical and preparative chiral chromatography is being able to control the order of enantiomer exit.

The three-dimensional glycosidic network of novel chiral supports thus offers this possibility through "matrix" effects, swelling to a greater or lesser extent depending on the degree of cross-linking of the support and the nature of the polar solvent used. Depending on the spatial disposition of the same functional constituents of each enantiomer, the matrix favours elution of one or other of the enantiomers by means of a variable three-dimensional structure.

The bifunctionality can bond chiral units, preferably glycosidic, via one or more covalent bonds to constitute a polymerised and cross-linked three-dimensional network and thus the degree of cross-linking depends on:

the number of —OH, —NH$_2$, —NHR or SH functions in the chiral unit which have reacted or react with compounds:

[R—CH=CH—X—O]$_n$Ar—Q

[(R$_1$, R$_2$, R$_3$)Si—CH(R)—CH$_2$—X—O]$_n$Ar—Q the number n of these same formulae where R, X, n, Ar, R$_1$, R$_2$, and R$_3$ are defined below.

The —OH, —NH$_2$ or SH functions are generally and preferably partially reacted to form derivatives in the case where polar solvents are to be used and to benefit from the "matrix" effects relating thereto. The degree of cross-linking of the network, preferably a three-dimensional chiral glycosidic network, is maximal and the swelling effects are also maximised; the use of gradient methods is generally impossible, as is the use of pure polar solvents or mixtures with high polar solvent contents.

BRIEF DESCRIPTION OF THE DRAWINGS

FIG. 1C depicts the separation on a type A support with a test solute of 2,2,2-trifluoro-1-(9-anthryl)ethanol.

FIG. 1D depicts the separation on a type A support with a test solute of indapamide.

METHODS OF THE INVENTION

Figure 1B:
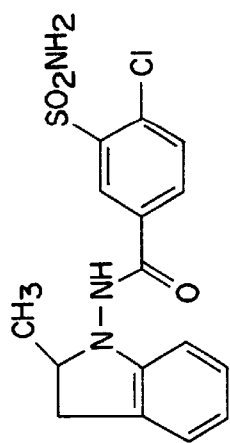
FIG. 1B depicts the separation on a type A support with a test solute of indapamide.
Figure 1B:
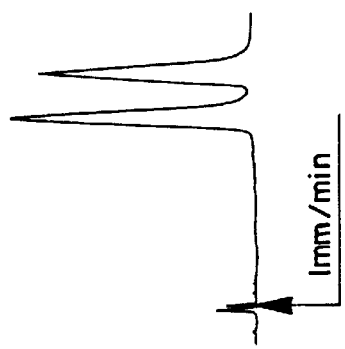

The invention provides a method comprising the following successive steps:

1) synthesis of at least one bifunctional alkenyloxyaryl or alkenylaryloxyaryl type compound with general formula [R—CH=CH—(X)—O]$_n$—Ar—Q, where Q is a group which reacts with a hydrogen carried by a heteroatom selected from the group formed by oxygen, nitrogen and sulphur or a precursor of such a group, and where:

n is in the range 1 to 20;

R is hydrogen or a linear or branched alkyl group or a linear or branched alkoxy group or a hydroxyl or an aryl group, which may be substituted;

X is a divalent linear alkyl group containing more than one carbon atom or a divalent branched alkyl group, or an aryl group, which may be substituted with at least one group selected from the group formed by hydrogen, alkyl, alkoxy, hydroxyl or trihalogenoalkyl groups;

Ar is a divalent aryl or polyaryl group, optionally substituted with at least one hydrogen atom or at least one group selected from the group formed by alkyl, alkoxy, hydroxyl, trihalogenoalkyl, silyl, thiol, amino, aminoalkyl, amide, nitro, nitrosamino, N-amino, aldehyde, acid or ester groups;

2) reacting at least one hydrogen of an alcohol, amine or thiol function of at least one chiral unit of a product, preferably a glycosidic unit of a product selected from holosides, heteroholisides, oligosides, cyclooligosides, heterooligosides, polyosides, heteropolyosides, enzymes and proteins with at least one group Q of the bifunctional compound of step 1), to synthesise at least one chiral compound.

The compound selected from holosides, heteroholosides, oligosides, cyclooligosides, heterooligosides, polyosides, heteropolyosides, enzymes and proteins is generally selected from the following compounds: pullulan, beta-2,1-fructan (inulin), beta-1,4-mannane, cellulose, beta-1,3-glucan curdlan, chitosan, dextran, amylose-cyclodextrins, alpha-1,3-glucan, beta-1,2-glucan, and beta-1,4-xylan, the formula for which are given below.

Group Q is preferably selected from the group formed by the following groups: —N=C=O or a precursor thereof; —NH$_2$, —CON$_3$ or —COCl or a precursor thereof; —COOH, —N=C=S, —CH$_2$—Y, where Y is Cl or Br or I or methylsulphonyloxy or paratoluenesulphonyloxy or 3,5-dimethylphenylsulphonyloxy.

The method of the invention may comprise a supplementary hydrosilylation step, before or after step 2), to transform at least a portion of the alkenyl moieties R—CH=CH— using a silane (R$_1$, R$_2$, R$_3$)Si—H generally in the presence of a metallic complex derived from platinum or rhodium to (R$_1$, R$_2$, R$_3$)—Si—CH(R)—CH$_2$— moieties, where:

R$_1$ is hydrogen or a methoxy or ethoxy group or a halogen or an amino or alkylamino group;

R$_2$ and R$_3$, which may be identical to or different from R$_1$, are alkoxy, hydroxyl, trihalogenoalkyl, linear or branched alkyl, or aryl groups;

R is hydrogen or a linear or branched alkyl group or a linear or branched alkoxy group or a hydroxyl group or an aryl group which may be substituted.

Hydrosilylation generally takes place in a solvent medium in the presence of a suitable catalyst such as platinum.

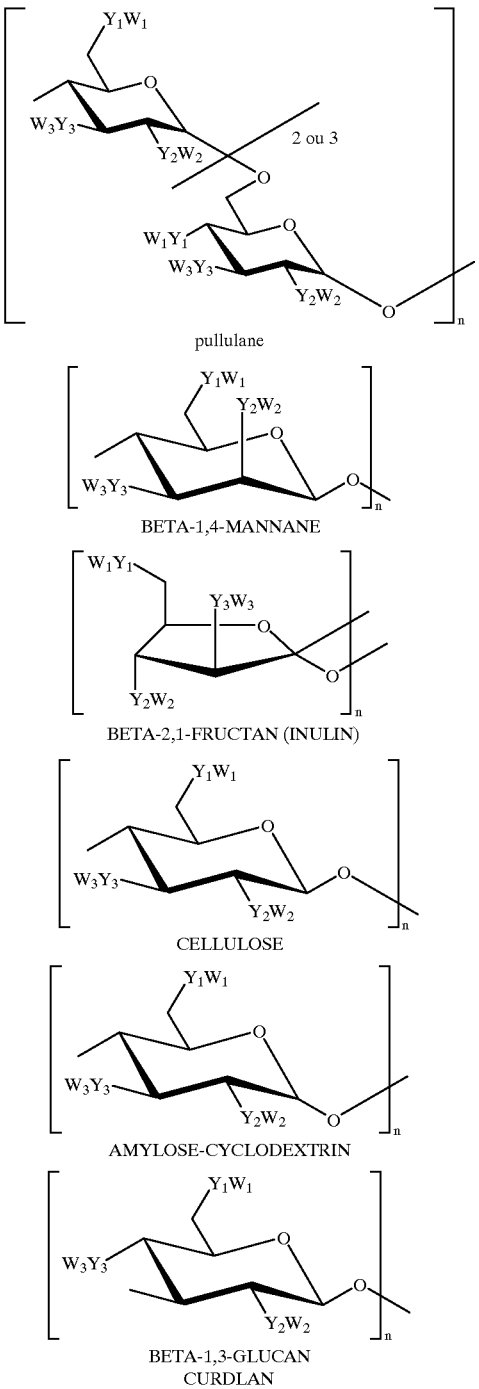

pullulane

BETA-1,4-MANNANE

BETA-2,1-FRUCTAN (INULIN)

CELLULOSE

AMYLOSE-CYCLODEXTRIN

BETA-1,3-GLUCAN CURDLAN

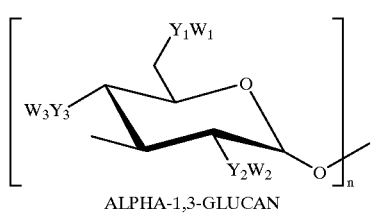
ALPHA-1,3-GLUCAN

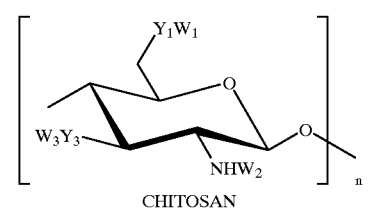
CHITOSAN

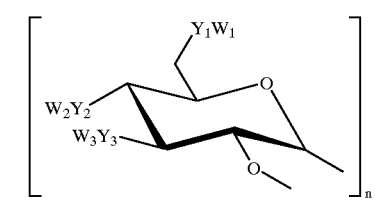
BETA-1,3-GLUCAN

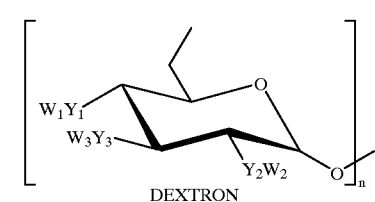
DEXTRON

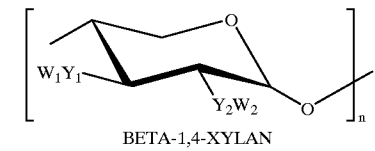
BETA-1,4-XYLAN

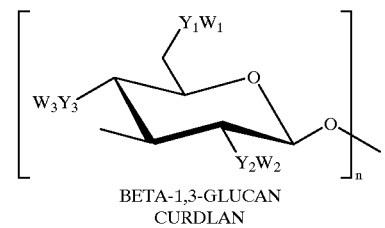
BETA-1,3-GLUCAN
CURDLAN

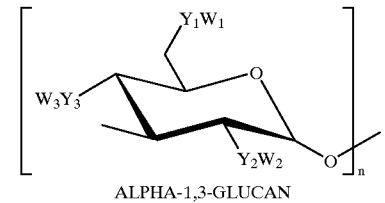
ALPHA-1,3-GLUCAN

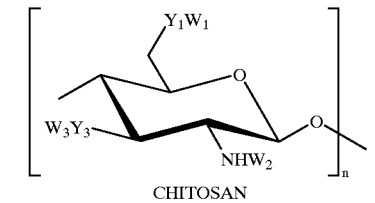
CHITOSAN

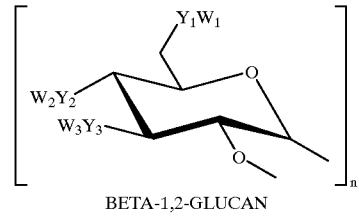
BETA-1,2-GLUCAN

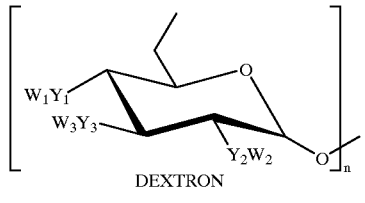
DEXTRON

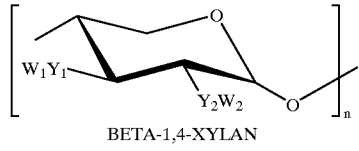
BETA-1,4-XYLAN where each Y ($Y_1$, $Y_2$ or $Y_3$) represents a sulphur or oxygen atom or the group NH;

each W ($W_1$, $W_2$ or $W_3$) represents an ethylenic radical with general formula [R—CH=CH—(X)—O]$_n$—Ar—Z— where Z represents a NH—CO group, or an —NH—CS group, or a CO group, or a $CH_2$ group;

and in which symbols R, X and Ar are defined below;

where n is a whole number in the range 5 to 2000;

and where each glycosidic unit contains at least 0.05 Y-W groups;

groups Y-W may be identical or different.

Polymerised and Cross Linked Clural Compounds

The invention particularly provides a polymerised and cross-linked chiral compound or ester, amide, urea, carbamate, thioester or thiocarbamate derivatives of said polymerised and cross-linked chiral compound, with general formula:

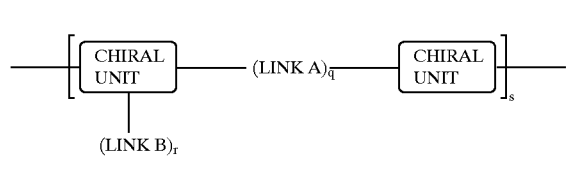

where:

q is at least 1 and less than 20;

s is at least 1 and less than 20000;

if r=0, the compound is a pure cross-linked chiral polymer, oligomer or monomer;

if r≧1, the compound is a chiral polymer, oligomer or monomer which is cross-linked in a three-dimensional network and bonded to a cross-linked support.

LINK A represents:

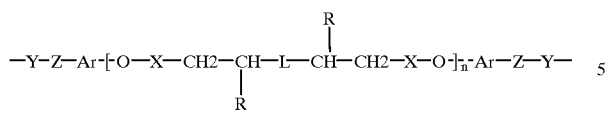

LINK B represents:

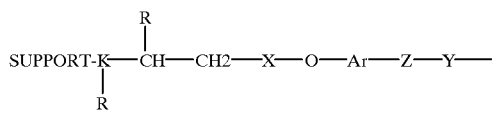

"chiral unit" represents a monomeric, oligomeric, cyclooligomeric or polymeric chiral compound and optionally comprises a primary or secondary amine function or a primary, secondary or tertiary hydroxyl function or a sulphhydryl function and in which all or a portion of these functions have optionally been modified to the ester, amide, urea, carbamate, thioester or thiocarbamate;

Z represents a —$CH_2$— group or a —CO— group or a —NH—CO— group or a —NH—CS— group;

Y represents a sulphur or oxygen atom or the amino group;

n is in the range 1 to 20;

Ar represents a divalent aryl or polyaryl group;

X represents a divalent alkyl or aryl group;

R represents an alkyl group or hydrogen;

L represents a single bond or a bis-sulphhydryl or silane or an ethylene group which may be substituted or a disiloxane;

K represents a single bond or a siloxane or a silane;

"support" represents an organic or mineral support; functionalised by an alkene or a hydrogenosilane or a sulphhydryl.

Thus the compound or one of its derivatives preferably has one of the following formulae:

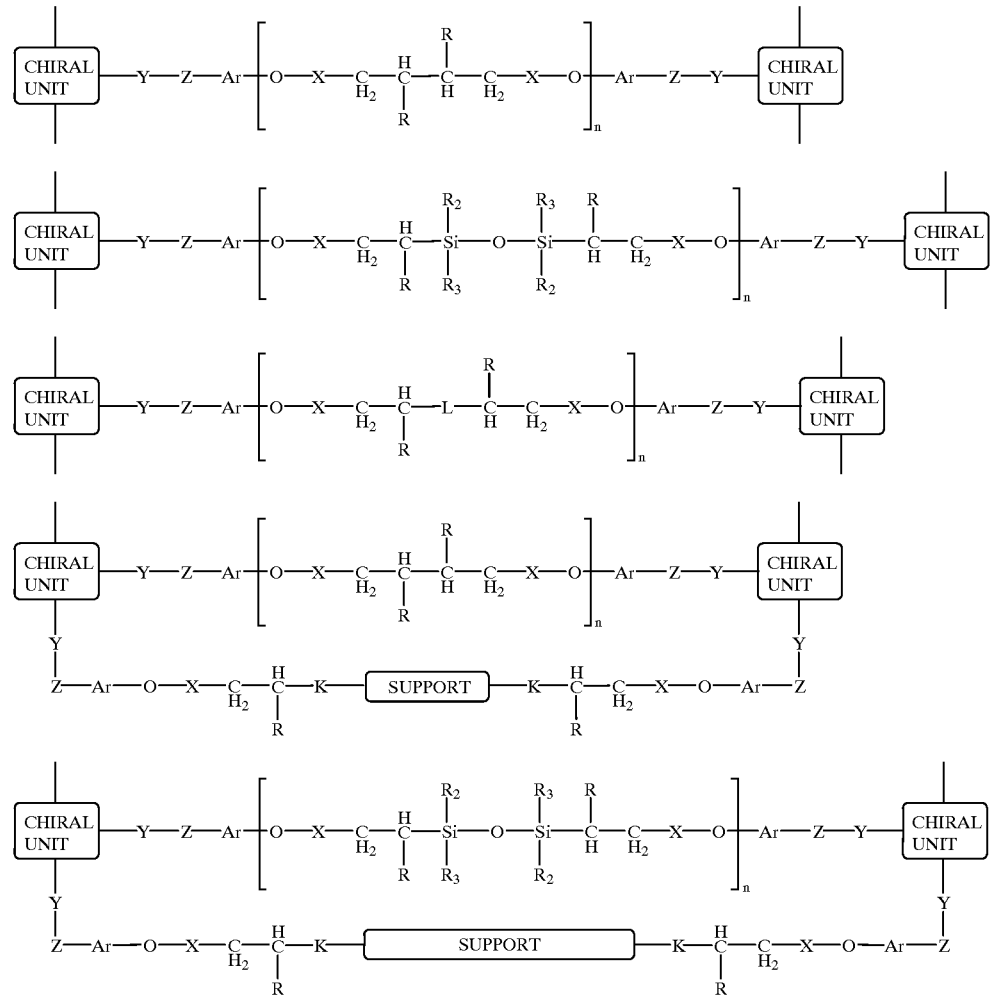

-continued

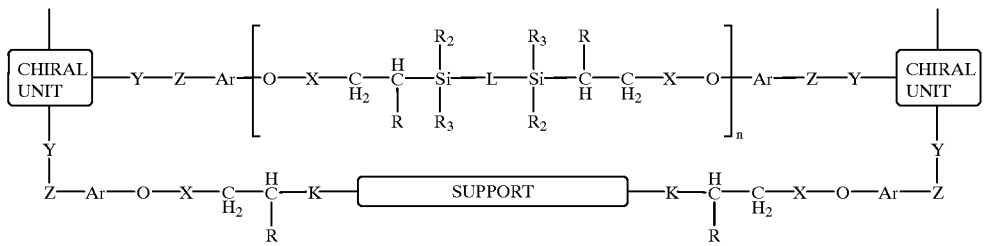

The method of the invention preferably comprises a supplementary step for treating at least a portion of the chiral compound obtained above to obtain a chiral support. The treatment is generally selected from the group formed by the three treatments described below.

A first treatment for the chiral compound consists of physical deposition of at least a portion of the compound on a support. Such a treatment generally consists of adding a co-solvent to the chiral compound which is dissolved in a polar solvent in the presence of a support, addition being followed by precipitation of the compound on the support, or evaporation of the chiral compound which is dissolved in a polar solvent in the presence of a support.

A second treatment for the chiral compound consists of physical deposition then grafting by covalently bonding at least part of the chiral compound onto a support, the support having been at least partially reacted with at least one group selected from the group formed by alkoxy, halogeno or aminosilane groups to form a derivative, the group also carrying a function of the type —SH, —SiH or —CH=CH—. The second treatment generally comprises adding free alkenyl functions of the portion of the chiral compound to the derivative support followed by in situ cross-linking of the remaining alkenyl functions to constitute a three-dimensional chiral network. The reaction is generally carried out in a solvent with a high boiling point such as a hydrocarbon, to encourage the kinetics. The grafting reaction between at least a portion of the alkenyl functions of the chiral units (preferably glycosidic) of the chiral compound and at least a portion of the —SH, —SiH or —CH=CH— functions of the derivative support generally takes place in an organic solvent in the presence of a suitable catalyst such as platinum salts or peroxides. When the chiral compound has undergone the supplemental hydrosilylation step, grafting is generally carried out on at least a portion of the hydrogen, alkoxy, halogeno or alkylaminosilane type terminal groups.

Regarding the first and second treatments, the support is generally selected from the group formed by gel type supports of native or modified silica, oxides of zirconia, magnesium, aluminium, or titanium, glass beads, carbons or any organic polymer.

A third treatment for the chiral compound consists of at least partial polymerisation, generally by cross-linking at least a portion of the chiral compound to obtain polymer beads which essentially constitute a chiral support. One possible manner of carrying out the third treatment generally comprises dissolving the portion of the chiral compound in a suitable solvent then reacting it in a two-phase medium, followed by evaporating the solvent to obtain a polymer in the form of beads or irregular particles, then polymerisation by intra- or inter-molecular cross-linking of at least a portion of the alkenyl moieties of the units, preferably glycosidic, of that portion of the chiral compound, by heating in the presence of a polymerisation initiator such as a peroxide. A further manner of carrying out the third treatment comprises the same steps, with the exception of polymerisation by cross-linking which is obtained by hydrosilylation, using hydrosilanes or hydrosiloxanes, of at least a portion of the alkenyl functions of that portion of the chiral compound on bifunctional dithiol type compounds HS—( . . . )—SH, dihydrogenosilanes HSi—( . . . )—SiH, or polyfunctional tetramethyldisiloxane, or 1,3,5,7-tetramethylcyclotetrasiloxane, or methylhydrocyclosiloxanes type compounds, or ethanediol type compounds or with sulphur.

Polymerisation by cross-linking is known per se and has been described, for example, in J. Chromatogr. 1992, 594, 283–290. The technique described in this article can be used to prepare the chiral compounds of the invention. In general, the reaction is carried out in a solvent which is inert towards hydrosilylation, such as toluene, 1,4-dioxane, chloroform, tetrahydrofuran (THE) or xylene, or mixtures of these solvents, at temperatures of 40° C. to 140° C. Using a catalyst such as metallic platinum or rhodium complexes accelerates the reaction kinetics.

The hydrosilanes or hydrosiloxanes used to prepare the chiral compounds can be defined by the following general formula:

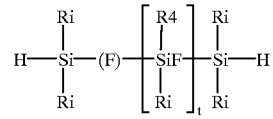

$R^4$: is an alkoxy, halogen or alkylamino group;

Ri: is identical to or different from $R_1$ and is an alkoxy, hydroxyl, aryl, halogen, alkylamino, trihalogenoalkyl, or linear or branched alkyl group;

F: is $(CH_2)_u$ or oxygen;

t: is 0 to 3000;

u: is 0 to 10.

When the chiral compound has undergone a supplemental hydrosilylation step, polymerisation principally occurs by controlled hydrolysis of at least a portion of the terminal hydrogenosilane, alkoxysilane, halogenosilane or N-alkylaminosilane type functions, which mainly results in substantially spherical particles of pure polymer.

The chiral support obtained above by one of the three treatments is preferably used in accordance with the method of the invention in an operation for separating chiral compounds or for preparing enantiomers. The operation is generally selected from the following methods: liquid chromatography, generally preparative or analytical liquid chromatography, comprising the following techniques: low, medium and high pressure (HPLC) liquid chromatography, counter-current chromatography and simulated moving bed chromatography, gas chromatography, generally analytical or preparative, supercritical chromatography, subcritical chromatography, centrifugal chromatography, electrophoresis, electrochromatography, or any membrane separation process, also asymmetrical synthesis.

Process for Synthesizing Polymers

The invention also provides a process for synthesising polymers comprising the following successive steps:
1) synthesising at least one bifunctional alkenyloxyaryl or alkenylaryloxyaryl type compound with general formula [R—CH=CH—X—O]$_n$Ar—Q,
    where Q is a group selected from the group formed by the following groups: —N=C=O or a precursor thereof, —NH$_2$ or —CON$_3$, —COCl or a precursor thereof, —COOH, —N=C=S, —CH$_2$Y, where Y is Cl or Br or I or methylsulphonyloxy or paratoluenesulphonyloxy or 3,5-dimethylphenylsulphonyloxy, and where:
    n is in the range 1 to 20;
    R is hydrogen or a linear or branched alkyl group or a linear or a branched alkoxy group or a hydroxyl or an aryl group, which may be substituted;
    X is a linear or branched alkyl group or an aryl group, which may be substituted with at least one group selected from the group formed by hydrogen, alkyl, alkoxy, hydroxyl and trihalogenoalkyl groups;
    Ar is an aryl or polyaryl group, which may be substituted with at least one hydrogen atom or a group selected from the group formed by alkyl, alkoxy, hydroxyl, trihalogenoalkyl, silyl, thiol, amino, aminoalkyl, amide, nitro, nitrosamino, N-amino, aldehyde, acid or ester groups;
2) polymerisation by the alkenyl moiety or by the R$_1$ group of the bifunctional compound of step 1), to synthesise at least one polymer functionalised by a group Q.

Bifunctional Compounds

The invention also provides any bifunctional alkenyloxyaryl or alkenylaryloxyaryl type compound with general formula [R—CH=CH—(X)—O]$_n$—Ar—Q,
    where Q is a group which is reactive towards a hydrogen carried by a heteroatom selected from the group formed by oxygen, nitrogen and sulphur, or a precursor of such a group, and where:
    n is in the range 1 to 20;
    R is hydrogen or a linear or branched alkyl group or a linear or branched alkoxy group or a hydroxyl or an aryl group, which may be substituted;
    X is an optional divalent linear or branched alkyl group or an aryl group, which may be substituted with at least one group selected from the group formed by hydrogen, alkyl, alkoxy, hydroxyl and trihalogenoalkyl groups;
    Ar is a divalent aryl or polyaryl group, which may be substituted with at least one hydrogen atom or with at least one group selected from the group formed by alkyl, alkoxy, hydroxyl, trihalogenoalkyl, silyl, thiol, amino, aminoalkyl, amide, nitro, nitrosamino, N-amino, aldehyde, acid or ester groups;
    excluding the following compounds: 4-allyloxyaniline, 4-allyloxybenzoic acid, its acid chloride, and 4-allyloxyphenylisocyanate. The synthesis and/or use of these compounds is described in the following articles:

M. A. Apfel, H. Finkelmann, G. M. Janini, R. J. Laub, B. H. Lehmann, A. Price, W. L. Roberts, T. J. Shaw and C. A. Smith, Analytical Chemistry, 1985, 57, 651–658;

Y. Nambu and T. Endo, Journal of Organic Chemistry, 1993, 58, 1932–1934;

G. Yi, J. S. Bradhsaw, B. E Rossiter, S. L. Reese, R. Petersson, K. E. Markides and M. L. Lee, Journal of Organic Chemistry, 1993, 58, 2561–2565;

G. Yi, J. S. Bradhsaw, N. E Rossiter, A. Malik, W. Li, H. Yun, M. L. Lee, Journal of Chromatography A, 673 (1994), 219–230;

G. Yi, J. S. Bradhsaw, B. E Rossiter, A. Malik, W. Li, H. Yun, M. L. Lee, Journal of Heterocyclic Chemistry, 352, 621 (1995);

G. Yi, W. Li, J. S. Bradhsaw, A. Malik, M. L. Lee, Journal of Heterocyclic Chemistry, 32, 1715 (1995).

Group Q is preferably selected from the group formed by the following groups: —N=C=O or a precursor thereof, —NH$_2$ or —CON$_3$, —COCl or its precursor, —COOH, —N=C=S, —CH$_2$Y, where Y is Cl or Br or I or methylsulphonyloxy or paratoluenesulphonyloxy or 3,5-dimethylphenylsulphonyloxy.

Chiral Compounds

The invention also provides any chiral compound which can be obtained by a substitution reaction of at least one hydrogen of an alcohol, amine or thiol function of at least one chiral unit of a product, preferably a glycosidic unit of a product selected from holosides, heteroholosides, oligosides, cyclooligosides, heterooligosides, polyosides, heteropolyosides, enzymes and proteins, with at least one group Q of the above bifunctional compound. The invention still further provides any chiral compound which can be obtained by hydrosilylation of the substituted chiral compound to transform at least a portion of the alkenyl moieties R—CH=CH— using a silane (R$_1$, R$_2$, R$_3$)Si—H generally in the presence of a metallic complex derived from platinum or rhodium to (R$_1$, R$_2$, R$_3$)Si—CH(R)—CH$_2$— moieties, where:
    R$_1$ is hydrogen or an alkoxy group or a halogen or an amino or alkylamino group;
    R$_2$ and R$_3$, which may be identical to or different from R$_1$, are alkoxy, hydroxyl, trihalogenoalkyl, linear or branched alkyl or aryl groups;
    R is hydrogen or a linear or branched alkyl group or a linear or branched alkoxy group or a hydroxyl group or an aryl group which may be substituted.

The invention yet still further provides any chiral compound which can be obtained by hydrosilylation of a bifunctional compound to transform at least a portion, of the alkenyl moieties R—CH=CH— using a silane (R$_1$, R$_2$, R$_3$)Si—H generally in the presence of a metallic complex derived from platinum or rhodium to (R$_1$, R$_2$, R$_3$)Si—CH (R)—CH$_2$— moieties, where:
    R$_1$ is hydrogen or an alkoxy group or a halogen or an amino or alkylamino group;
    R$_2$ and R$_3$, which may be identical to or different from R$_1$, are alkoxy, hydroxyl, trihalogenoalkyl, linear or branched alkyl or aryl groups;
    R is hydrogen or a linear or branched alkyl group or a linear or branched alkoxy group or a hydroxyl group or an aryl group which may be substituted;
then by reacting at least one hydrogen of an alcohol, amine or thiol function of at least one chiral unit of a product, preferably a glycosidic unit of a product selected from holosides, heteroholisides, oligosides, cyclooligosides, heterooligosides, polyosides, heteropolyosides, enzymes and proteins, with at least one group Q of the above bifunctional compound.

Chiral Support

The invention also provides any chiral support which can be obtained from the preceding chiral compounds by physical deposition on a support. The invention also provides any chiral support which can be obtained from the above chiral compounds and a support, the support having being derived from at least one group selected from the group formed by alkoxy, halogeno or aminosilane groups also comprising a —SH, —SiH or —CH=CH— type function, by forming covalent chemical bonds with at least a portion of the alkenyl moieties of said chiral compounds followed by in situ cross-linking of the remaining alkenyl functions to constitute a three-dimensional chiral network.

More generally, the invention provides any chiral support comprising at least one of the above chiral compounds and at least one support. The compound is preferably chemically bonded to the support, by at least one covalent chemical bond.

The support is generally selected from the group formed by gel type supports of native or modified silica, oxides of zirconia, magnesium, aluminium or titanium, glass beads, carbons or any organic polymer.

The invention also provides any chiral support which can be obtained from at least one of the above chiral compounds by polymerisation generally by cross-linking at least a portion of the alkenyl moieties of said chiral compound to obtain polymer beads.

More generally, the invention provides any chiral support comprising beads of at least one of the above chiral compounds.

Finally, the invention provides any process for separating chiral compounds or for preparing enantiomers using at least one chiral support as above in an operation selected from the following methods: liquid chromatography, gas chromatography, supercritical chromatography, subcritical chromatography, centrifugal chromatography, electrophoresis, electrochromatography, or any membrane separation process, also asymmetrical synthesis.

The following examples illustrate the invention without in any way limiting its scope.

EXAMPLES

1. Preparation of Chromatographic Supports in Accordance with the Invention a) Preparation of Parapent-4-enoxybenzoic Acid:

2 g of sodium hydroxide, 15 ml of distilled water, 7.6 g of methyl 4-hydroxybenzoate, 0.16 g of tetrabutylammonium bromide and 5.92 ml of 5-bromopent-1-ene were successively placed in a reactor. Vigorous stirring was maintained overnight at ambient temperature. After adding 30 ml of a 2.5 M sodium hydroxide solution, the reaction medium was heated to 60–80° C. for 90 minutes. It was then diluted with 120 ml of distilled water and extracted with two times 50 ml of diethyl ether. The aqueous phase was acidified with 10 ml of concentrated hydrochloric acid to precipitate the acid. After filtering, washing with distilled water and drying in a dessicator over $P_2O_5$, the acid was obtained in a yield of 93%.

b) Preparation of the Acid Chloride of Parapent-4-enoxybenzoic Acid:

10.3 g of parapent-4-enoxybenzoic acid was suspended in 60 ml of toluene to which 17 ml of thionyl chloride was added. The reaction mixture was heated under reflux for 30 minutes then vacuum evaporated. The oily residue obtained was vacuum distilled (110° C./1 mm of Hg). The yield from this synthesis was 85%.

c) Preparation of Parapent-4-enoxybenzoylazide:

A solution of 11.27 g of parapent-4-enoxybenzoyl chloride dissolved in 15 ml of acetone was added dropwise to an aqueous solution of sodium nitride (3.9 g in 22 ml of distilled water) at ambient temperature with vigorous stirring. Following addition, the reaction medium was stirred for one hour then diluted with 50 ml of water. After decanting, the colourless oil obtained was dried over magnesium sulphate. (Yield=80%).

d) Preparation of Parapent-4-enoxyphenylisocyanate 11.6 g of parapent-4-enoxybenzoylazide was dissolved in 80 ml of anhydrous toluene then heated under reflux for 90 min. The solvent was then vacuum evaporated and the residue which had the appearance of a colourless oil was vacuum distilled (100° C./1 mm of Hg). The yield from this synthesis was 94%.

a) Preparation of a Tris[3,6-(4-allyloxyphenyl)urethane] Cellulose (for Preparation of a type B support):

2.5 g of microcrystalline cellulose, 75 ml of pyridine and 38 ml of heptane were placed in a reactor. Stirring and heating the reaction mixture dehydrated the cellulose by azeotropic entrainment. 9.31 g of 4-allyloxyphenylisocyanate and 0.05 g of 4-dimethylaminopyridine were added to the mixture and it was heated under reflux for 8 hours. At the end of the reaction, 65 ml of methanol was added and refluxing was continued for 15 minutes. The cellulose derivative was then washed three times with 300 ml of distilled water then 140 ml of methanol.

b) Preparation of a Tris[6-(4-allyloxyphenyl)urethane-2,3,6-(3,5-dimethyalhenyl)urethane]Cellulose (for the preparation of a type A support)

2.5 g of microcrystalline cellulose, 75 ml of pyridine and 38 ml of heptane were placed in a reactor. Stirring and heating the reaction mixture dehydrated the cellulose by azeotropic entrainment. 1.35 g of 4-allyloxyphenylisocyanate, 6.80 g of 3,5-dimethylphenylisocyanate and 0.05 g of 4-dimethylaminopyridine were added to the mixture and it was heated under reflux for 8 hours. At the end of the reaction, 65 ml of methanol was added and refluxing was continued for 15 minutes. The cellulose derivative was then washed three times with 300 ml of distilled water then 140 ml of methanol.

3. Composite Obtained Between a Cellulose Derivative and a Modified Silica (mercaptopropyl silica)

a) Preparation of a Mercaptopropyl Silica 10 g of Kromasil silica (5 μm, 100- where 1.0=0.1 nm) suspended in 50 ml of toluene was placed in a reactor. The medium was heated under reflux to dehydrate the silica by azeotropic entrainment. 45 ml of mercaptopropyltrimethoxysilane and 20 ml of pyridine were then added. The reaction mixture was stirred and heated at 100° C. for two days. After filtering and washing with methanol and diethylether then vacuum drying at 60° C., a mercaptopropyl silica was obtained with a degree of grafting of 0.85 mmol/g of thiol function.

b) Preparation of Composite b1) For B type support: 0.45 g of tris[2,3,6-(4-allyloxyphenyl)urethane] cellulose was dissolved in 27 ml of tetrahydrofuran, then 3 g of Kromasil mercaptopropyl silica was added. After ultrasound degassing for three minutes, it was evaporated to dryness. The composite formed was filtered, then dried in the open air.

B2) For an A type support: 0.45 g of tris[6-(4-allyloxyphenyl)urethane-2,3,6-(3,5-dimethylphenyl)

urethane] cellulose was dissolved in 27 ml of tetrahydrofuran, then 3 g of mercaptopropyl Kromasil silica was added. After ultrasound degassing for three minutes, it was evaporated to dryness. The composite formed was filtered, then dried in the open air.

a) Preparation of a Type A Chromatographic Support:

The composite prepared as above (3-b2) was dissolved in 17 ml of heptane in the presence of a catalytic quantity of benzoyl peroxide. The reaction medium was heated under reflux for 14 hours then filtered and air dried.

b) Preparation of a Type B Chromatographic Support:

The composite prepared as above (3-b1) was dissolved in 17 ml of heptane in the presence of a catalytic quantity of benzoyl peroxide. The reaction medium was heated under reflux for 14 hours then filtered and air dried.

B—USE OF CHROMATOGRAPHIC SUPPORTS IN ACCORDANCE WITH THE INVENTION

IA—Example of Separation on a Type A Support

Figure 1A:
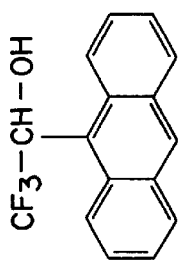
FIG. 1A depicts the separation on a type A support with a test solute of 2,2,2-trifluoro-1-(9-anthryl)ethanol.
Figure 1A:
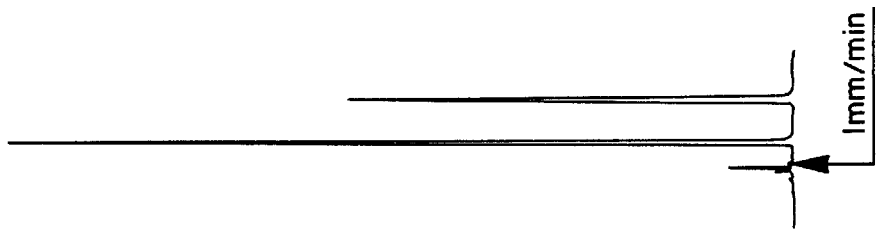

Test solute: 2,2,2-trifluoro-1-(9-anthryl)ethanol
Please refer to FIG. 1A

Mobile Phase: 100% Pure Chloroform
    UV detection at 254 nm; O. D. (optical density)=0.2
    Flow rate: 1 ml/min=P6.2 MPa (600 psi)°
    $T_0$=2.95" (non-retained solute transit time measured using 1,3,5,tritert-butylbenzene)
    Partition ratios: $k'_1$=1.03 $k'_2$=2.56
    ↑: $t_0$ injection
    Relative retention ratio: α=2.64

IB—Example of Separation on a Type A Support

Test Solute: Indapamide
Please refer to FIG. 1B

Mobile Phase: 100% Pure Chloroform
    UV detection at 254 nm; O. D.=0.2
    Flow rate: 1 ml/min P=6.2 MPa (600 psi)°
    $T_0$=2.95' (non-retained solute transit time measured using 1,3,5,tritert-butylbenzene)
    Partition ratios: $k'_1$=7.47 $k'_2$=9.17
    ↑: $t_0$ injection
    Relative retention ratio: α=1.23

IC—Example of Separation on a Type A Support

Test solute: 2,2,2-trifluoro-1-(9-anthryl)ethanol
Please refer to FIG. 1C

Mobile Phase: 100% Pure Dichloromethane
    UV detection at 254 nm; O. D.=0.2
    Flow rate: 1 ml/min P=6.2 MPa (600 psi)°
    $T_0$=2.95' (non-retained solute transit time measured using 1,3,5,tritert-butylbenzene)
    Partition ratios: $k'_1$=0.56 $k'_2$=1.03
    ↑: $t_0$ injection
    Relative retention ratio: α=1.85

ID—Example of Separation on a Type A Support

Test Solute: Indapamide

Mobile Phase: 100% Pure Dichloromethane
    UV detection at 254 nm; O. D.=0.2
    Flow rate: 1 ml/min P=6.2 MPa (600 psi)°
    $T_0$=2.95' (non-retained solute transit time measured using 1,3,5,tritert-butylbenzene)
    Partition ratios: $k'_1$=2.13 $k'_2$=2.39
    ↑: $t_0$ injection
    Relative retention ratio: α=1.12

IE—Example of Separation on a Type B Support

Figure 1E:
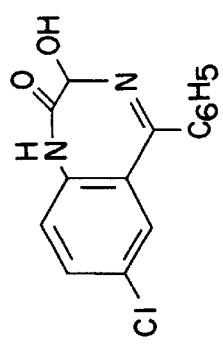
FIG. 1E depicts the separation on a type B support with a test solute of oxazepam.
Figure 1E:

Test Solute: Oxazepam
Please refer to FIG. 1E

Mobile Phase: 70/30/0.1 Heptane/isoyropanol/diethylamine
    UV detection at 254 nm; O. D.=0.1
    Flow rate: 1 ml/min P=5.5 MPa (800 psi)°
    $T_0$=2.82' (non-retained solute transit time measured using 1,3,5,tritert-butylbenzene)

Partition ratios: $k'_1=2.69$ $k'_2=10.18$

↑t: $t_0$ injection

Relative retention ratio: $\alpha=3.78$

IIA—Example of Separation on a Type A Support

Test Solute: Indapamide

Figure 2A:
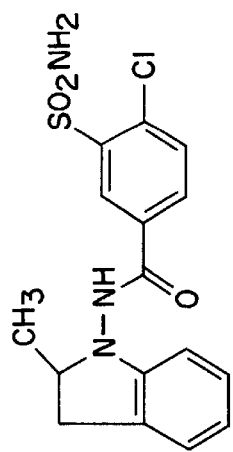
FIG. 2A depicts the separation on a type A support with a test solute of indapamide.
Figure 2A:
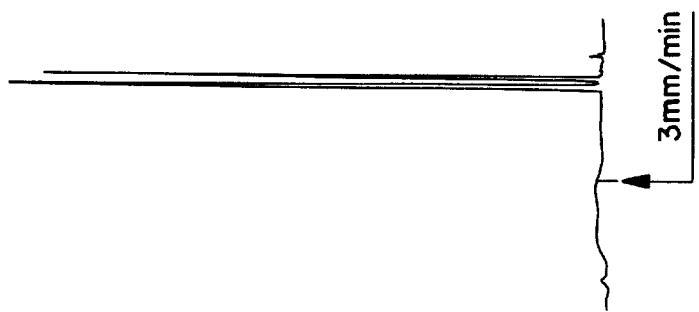

Please refer to FIG. 2A

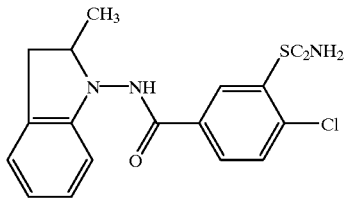

Mobile Phase: Reverse Mode Elution Gradient Water (100%) to Acetonitrile (100%) in 60 Minutes UV detection at 254 nm; O. D.=0.5

Flow rate: 1 ml/min $T_0=2.80'$ (non-retained solute transit time measured using 1,3,5,tritert-butylbenzene)

Partition ratios: $k'_1=11.03$ $k'_2=11.58$

↑: $t_0$ injection

Relative retention ratio: $\alpha=1.05$

IIB—Example of Separation on a Type A Support

Test Solute: Benzoin

Figure 2B:
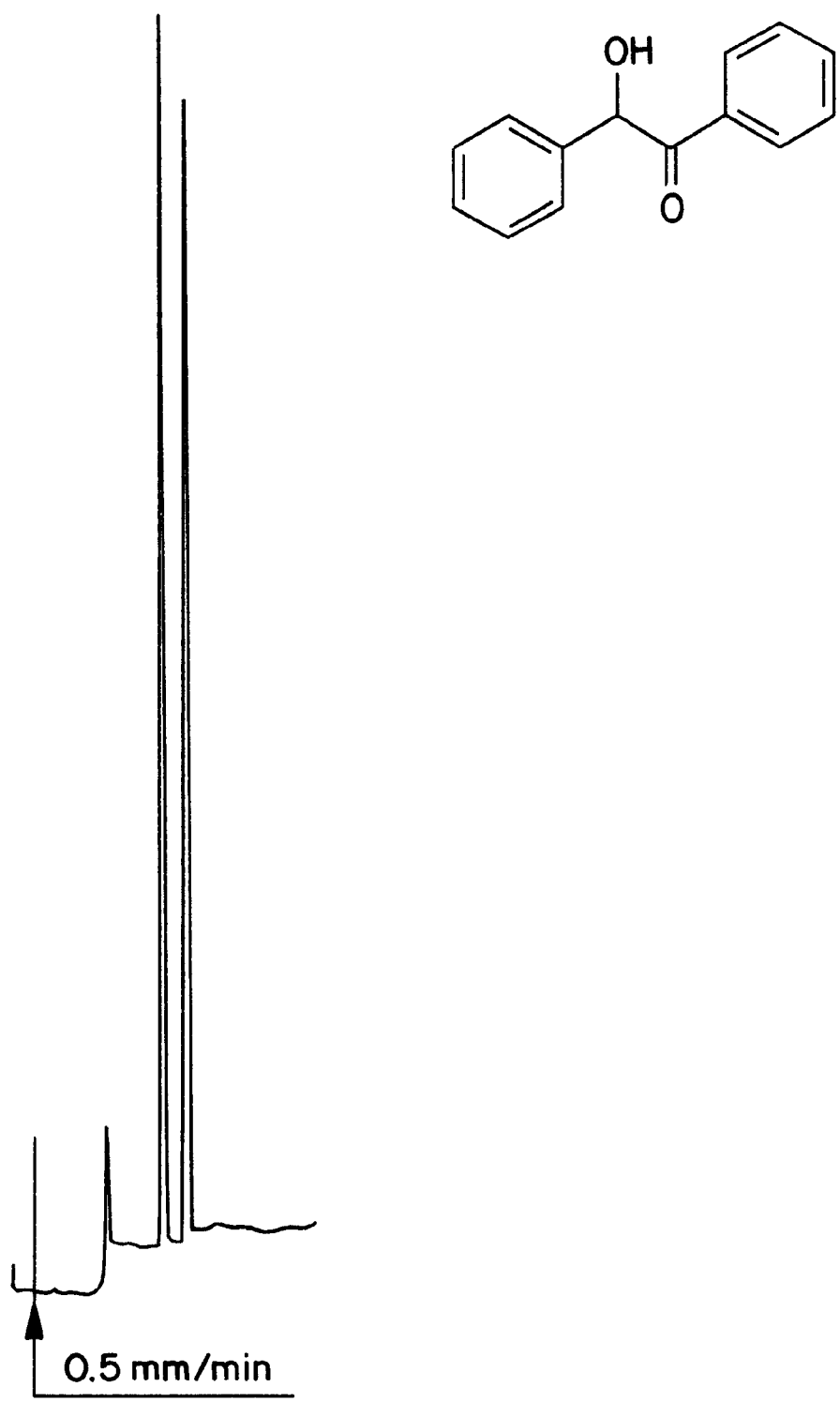
FIG. 2B depicts the separation on a type A support with a test solute of benzoin.

Please refer to FIG. 2B

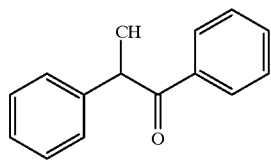

Mobile Phase: Normal Mode Elution Gradient Heptane (100%) to Isopropanol (100%) in 60 Minutes 20 UV detection at 254 nm; O. D.=0.02

Flow rate: 1 ml/min $T_0=2.90'$ (non-retained solute transit time measured using 1,3,5,tritert-butylbenzene)

Partition ratios: $k'_1=5.10$ $k'_2=6.28$

↑: $t_0$ injection

Relative retention ratio: $\alpha=1.23$

III: Example of Inversion of Order of Exit of Enantiomers of an Active Pharmaceutical Ingredient on a Type A Support Active Ingredient (eutomer): 17454

Unwanted Enantiomer (distomer): 17455

CONDITIONS 2: 17455 Eluted before 17454

Mobile Phase:

| | |
|---|---|
| heptane + 2% diethylamine | 10% |
| dichloromethane | 22% |
| heptane | 66% |
| methanol | 2% |

-continued

| | |
|---|---|
| Retention time of S 17455: | 13.86' |
| Retention time of S 17454: | 14.93' |
| (see diagram below) | |

Other parameters for conditions 1 and conditions 2 were identical, namely:

detection wavelength: 270 nm, UV flow rate: 1 ml/min

20 μl volume injected, i.e., 20 μg of solute at the concentration used.

III continued

CONDITIONS 1

Figure 3A:
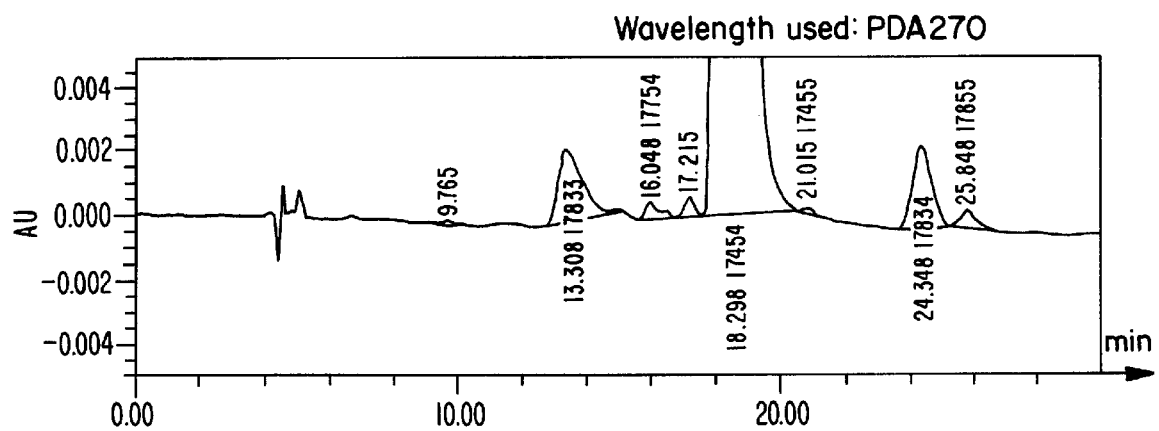
FIG. 3A depicts the inversion exit order of enantiomers of an active pharmaceutical ingredient on a type A support eluted after 17454.
Figure 3B:
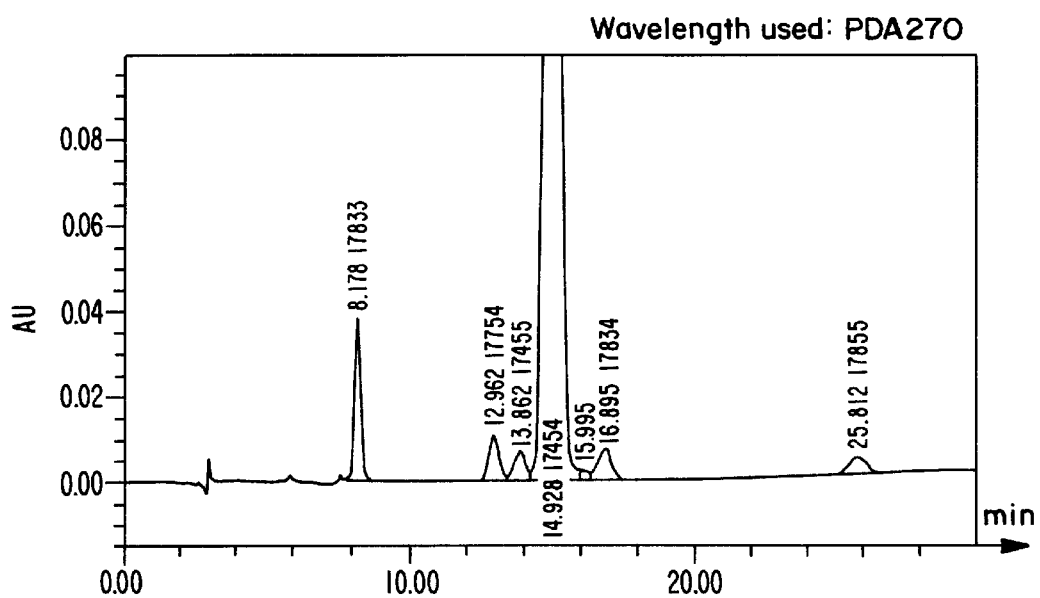
FIG. 3B depicts the inversion exit order of enantiomers of an active pharmaceutical ingredient on a type A support eluted before 17454.

Please refer to FIG. 3A and 3B

The foregoing examples can be repeated with analogous results by substituting the reactants and/or the general or particular conditions described in the invention for those used in the examples.

In the light of the above description, the skilled person can readily determine the essential characteristics of the invention and could make various changes and modifications without departing from the spirit and scope of the invention, to adapt it to various uses and conditions for carrying out the invention.

What is claimed is:

1. A chiral compound obtained by reaction of at least one hydrogen of an alcohol, amine, or thiol function of at least one chiral unit of a product with at least one group Q of a bifunctional alkenoxyaryl or alkenylaryloxyaryl type compound with formula $(R-CH=CH-(X)-O)_n-Ar-Q$, where Q is $-N=C=O$ or a precursor thereof; $-NH_2$ or $-CON_3$; $-COCl$ or its precursor; $-COOH$; $-N=C=S$; or $-CH_2Y$, where Y is Cl or Br or I or methylsulphonyloxy or paratoluenesulphonyloxy or 3,5-dimethylphenylsulphonyloxy and where:

n is in the range 1 to 20;

R is hydrogen or a linear or branched alkyl group or a linear or branched alkoxy group or hydroxyl or an aryl group, optionally substituted;

X is a linear alkyl group carrying more than one carbon atom or a branched alkyl group, or an aryl group, optionally substituted with at least one group selected from the group consisting of hydrogen, alkyl, alkoxy, hydroxyl and trihalogenoalkyl groups; and Ar is an aryl or polyaryl group, optionally substituted with at least one hydrogen atom or with at least one group selected from the group consisting of alkyl, alkoxy, hydroxyl, trihalogenoalkyl, silyl, thiol, amino, aminoalkyl, amide, nitro, nitrosamino, N-amino, aldehyde, acid and ester groups, excluding the following compounds: 4-allyloxyaniline, 4-allyloxybenzoic acid, its acid chloride, and 4-allyloxyphenylisocyanate.

2. A chiral compound which can be obtained by hydrosilylation of the chiral compound of claim 1 to transform at least a portion of the alkenyl moieties $R-CH=CH-$ using a silane $(R_1, R_2, R_3)Si-H$ generally in the presence of a metallic complex derived from platinum or rhodium to $(R_1, R_2, R_3)-Si-CH(R)-CH_2-$ moieties, where:

$R_1$ is hydrogen or an alkoxy group or a halogen or an amino or alkylamino group;

$R_2$ and $R_3$, which may be identical to or different from $R_1$, are alkoxy, hydroxyl, trihalogenoalkyl, linear or branched alkyl or aryl groups;

R is hydrogen or a linear or branched alkyl group or a linear or branched alkoxy group or a hydroxyl group or an aryl group optionally substituted.

3. A chiral compound which can be obtained by hydrosilylation of the bifunctional alkenyloxyaryl or alkenylaryloxyaryl type compound with formula (R—CH=CH—(X)—O)$_n$—Ar—Q, where Q is —N=C=O or a precursor thereof: —NH$_2$ or —CON$_3$; —COCl or its precursor;

—COOH; —N=C=S; or —CH$_2$Y, where Y is Cl or Br or I or methylsulphonyloxy or paratoluenesulphonyloxy or 3,5-dimethylphenylsulphonyloxy and where:

n is in the range 1 to 20;

R is hydrogen or a linear or branched alkyl group or a linear or branched alkoxy group or hydroxyl or an aryl group, optionally substituted;

X is a linear alkyl group carrying more than one carbon atom or a branched alkyl group, or an aryl group, optionally substituted with at least one group selected from the group consisting of hydrogen, alkyl, alkoxy, hydroxyl and trihalogenoalkyl groups; and Ar is an aryl or polyaryl group, optionally substituted with at least one hydrogen atom or with at least one group selected from the group consisting of alkyl, alkoxy, hydroxyl, trihalogenoalkyl, silyl, thiol, amino, aminoalkyl, amide, nitro, nitrosamino, N-amino, aldehyde, acid and ester groups, excluding the following compounds: 4-allyloxyaniline, 4-allyloxybenzoic acid, its acid chloride, and 4-allyloxyphenylisocyanate to transform at least a portion of alkenyl moieties R—CH+CH— using a silane (R$_1$, R$_2$, R$_3$)—Si—H in the presence of a metallic complex derived from platinum or rhodium to (R$_1$, R$_2$, R$_3$)—Si—CH(R)—CH$_2$— moieties, where:

R$_1$ is hydrogen or an alkoxy group or a halogen or an amino or alkylamion group;

R$_2$ and R$_3$, which may be identical to or different from R$_1$, are alkoxy, hydroxyl, trihalogenoalkyl, linear or branched alkyl or aryl groups;

then by reacting at least one hydrogen of an alcohol, amine or thiol function of at least one chiral unit of a product with at least one group Q of the hydrosilylated bifunctional alkenyloxyaryl or alkenylaryloxyaryl type compound.

4. A chiral compound according to claim 1, in which said chiral unit of a product is a glycosidic unit of a product selected from holosides, heterobolosides, oligosides, cyclooligosides, heterooligosides, polyosides, heteropolyosides, enzymes and proteins.

5. A chiral compound according to claim 2, wherein the bifunctional compound is parapent-4-enoxybenzoic acid.

6. A chiral compound according to claim 1, wherein the bifunctional compound is selected from the group consisting of parapent-4-enoxybenzoic acid, the acid chloride thereof, parapent-4-enoxybenzoylazide, and parapent-4-enoxyphenylisocyanate.

7. A chiral compound according to claim 5, wherein the bifunctional compound is parapent-4-enoxybenzoic acid.

8. A chiral compound according to claim 1, wherein the bifunctional compound is parapent-4-enoxybenzoic acid.

9. A chiral compound according to claim 4, wherein the bifunctional compound is parapent-4-enoxybenzoic acid.

10. A chiral compound according to claim 2, in which said chiral unit of a product is a glycosidic unit of a product selected from holosides, heteroholosides, oligosides, cyclooligosides, heterooligosides, polyosides, heteropolyosides, enzymes and proteins.

11. A chiral compound according to claim 3, in which said chiral unit of a product is a glycosidic unit of a product selected from holosides, heteroholosides, oligosides, cyclooligosides, heterooligosides, polyosides, heteropolyosides, enzymes and proteins.

12. A chiral compound obtained by hydrosilylation of another chiral compound obtained by reaction of at least one hydrogen of an alcohol, amine, or thiol function of at least one chiral unit of a product with at least one group Q of a bifunctional compound wherein the bifunctional compound is an alkenyloxyaryl or alkenylaryloxyaryl type compound with formula (R—CH=CH—(X)—O)$_n$—Ar—Q, where Q is —N=C=O or a precursor thereof; —NH$_2$ or —CON$_3$; —COCl or its precursor; —COOH; —N=C=S; or —CH$_2$Y, where Y is Cl or Br or I or methylsulphonyloxy or paratoluenesulphonyloxy or 3,5-dimethylphenylsulphonyloxy and where:

n is in the range 1 to 20;

R is hydrogen or a linear or branched alkyl group or a linear or branched alkoxy group or hydroxyl or an aryl group, optionally substituted;

X is a linear alkyl group carrying more than one carbon atom or a branched alkyl group, or an aryl group, optionally substituted with at least one group selected from the group consisting of hydrogen, alkyl, alkoxy, hydroxyl and trihalogenoalkyl groups; and Ar is an aryl or polyaryl group, optionally substituted with at least one hydrogen atom or with at least one group selected from the group consisting of alkyl, alkoxy, hydroxyl, trihalogenoalkyl, silyl, thiol, amino, aminoalkyl, amide, nitro, nitrosamino, N-amino, aldehyde, acid and ester groups, excluding the following compounds: 4-allyloxyaniline, 4-allyloxybenzoic acid, its acid chloride, and 4-allyloxyphenylisocyanate; wherein, the reaction transforms at least a portion of the alkenyl moieties R—CH=CH— using a silane (R$_1$, R$_2$, R$_3$)—Si—H in the presence of a metallic complex derived from platinum or rhodium to (R$_1$, R$_2$, R$_3$)—Si—CH(R)—CH$_2$— moieties, where:

R$_1$ is hydrogen or an alkoxy group or a halogen or an amino or alkylamino group;

R$_2$ and R$_3$, which may be identical to or different from R$_1$, are alkoxy, hydroxyl, trihalogenoalkyl, linear or branched alkyl or aryl groups; and R is hydrogen or a linear or branched alkyl group or a linear or branched alkoxy group or a hydroxyl group or an aryl group optionally substituted.

13. The chiral compound according to claim 12 in which said chiral unit of a product is a glycosidic unit of a product selected from holosides, heteroholosides, oligosides, cyclooligosides, heterooligosides, polyosides, heteropolyosides, enzymes and proteins.

14. The chiral compound according to claim 12 wherein the bifunctional compound is selected from the group consisting of parapent-4-enoxybenzoic acid, the acid chloride thereof, parapent-4-enoxybenzoylazide, and parapent-4-enoxyphenylisocyanate.

15. The chiral compound according to claim 12, wherein the bifunctional compound is parapent-4-enoxybenzoic acid.

16. The chiral compound according to claim 13, wherein the bifunctional compound is parapent-4-enoxybenzoic acid.

17. The chiral compound according to claim 14, in which said chiral unit of a product is a glycosidic unit of a product selected from holosides, heteroholosides, oligosides, cyclooligosides, heterooligosides, polyosides, heteropolyosides, enzymes and proteins.

18. A compound according to claim 10, wherein the bifunctional compound is parapent-4-enoxybenzoic acid.

19. The chiral compound according to claim 6, in which said chiral unit of a product is a glycosidic unit of a product selected from holosides, heteroholosides, oligosides, cyclooligosides, heterooligosides, polyosides, heteropolyosides, enzymes and proteins.

20. The chiral compound according to claim 3, wherein the bifunctional compound is selected from the group consisting of parapent-4-enoxybenzoic acid, the acid chloride thereof, parapent-4-enoxybenzoylazide, and parapent-4-enoxyphenylisocyanate.

21. The chiral compound according to claim 11, wherein the bifunctional compound is parapent-4-enoxybenzoic acid.

22. The chiral compound according to claim 20, in which said chiral unit of a product is a glycosidic unit of a product selected from holosides, heteroholosides, oligosides, cyclooligosides, heterooligosides, polyosides, heteropolyosides, enzymes and proteins.

23. The chiral compound according to claim 2 wherein the bifunctional compound is selected from the group consisting of parapent-4-enoxybenzoic acid, the acid chloride thereof, parapent-4-enoxybenzoylazide, and parapent-4-enoxyphenylisocyanate.

24. The chiral compound according to claim 23, in which said chiral unit of a product is a glycosidic unit of a product selected from holosides, heteroholosides, oligosides, cyclooligosides, heterooligosides, polyosides, heteropolyosides, enzymes and proteins.

* * * * *

UNITED STATES PATENT AND TRADEMARK OFFICE
CERTIFICATE OF CORRECTION

| | | |
|---|---|---|
| PATENT NO. | : 6,342,592 B1 | Page 1 of 1 |
| APPLICATION NO. | : 09/039266 | |
| DATED | : January 29, 2002 | |
| INVENTOR(S) | : Raphael Duval | |

It is certified that error appears in the above-identified patent and that said Letters Patent is hereby corrected as shown below:

Column 20, line 60, reads "generally in" should read -- in --
Column 21, line 31, begin new line at "to transform"
Column 21, line 38, reads "alkylmion" should read -- alkylamino --
Column 21, line 49, reads "heterobolosides," should read -- heteroholosides, --
Column 21, line 59, reads "according to claim 5," should read -- according to claim 3, --

Signed and Sealed this

Seventeenth Day of July, 2007

JON W. DUDAS
*Director of the United States Patent and Trademark Office*